Feb. 13, 1962 E. S. BOERNER Plant Pat. 2,130
ROSE PLANT
Filed March 23, 1961
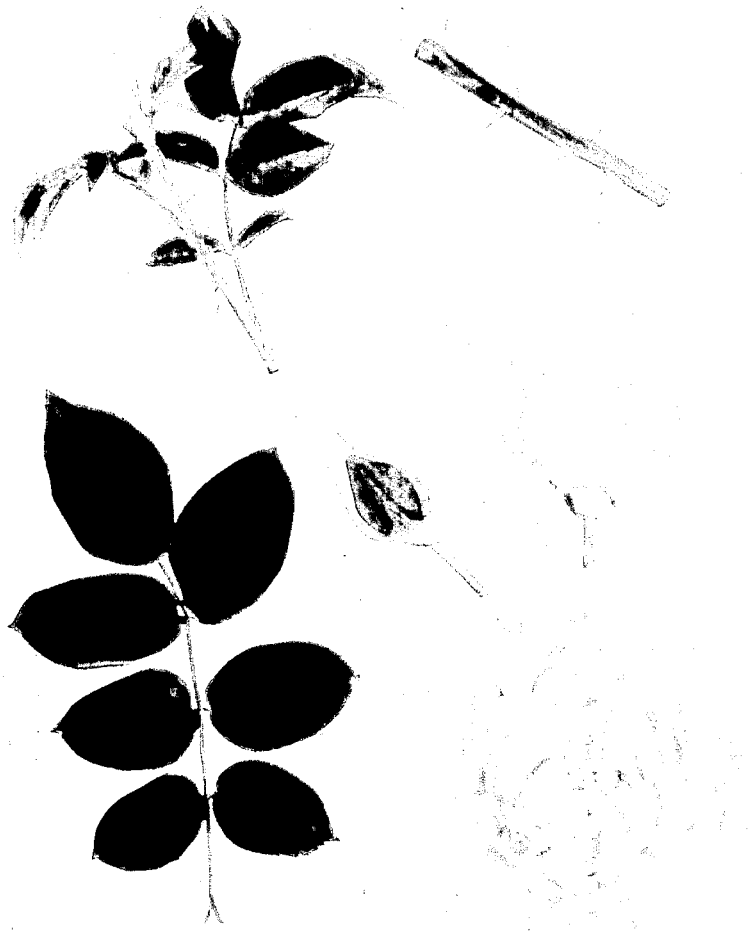
Inventor.
E. S. Boerner
By: Robb & Robb
Attorneys.

United States Patent Office

Plant Pat. 2,130
Patented Feb. 13, 1962

2,130
ROSE PLANT

Eugene S. Boerner, Newark, N.Y., assignor, by mesne assignments, to Home Nursery Products Corporation, Newark, N.Y., a corporation of New York Filed Mar. 23, 1961, Ser. No. 97,981
1 Claim. (Cl. 47—61)

The present invention relates to a new and distinct variety of rose plant of the floribunda class, which was originated by me by crossing an unnamed and unpatented seedling derived from a cross of "Geranium Red" (Plant Patent No. 811) × "Fashion" (Plant Patent No. 789) with another unnamed and unpatented seedling derived from a cross of "Diamond Jubilee" (Plant Patent No. 824) × "Fashion."

The primary objective of this breeding was to produce a new rose variety of a hardy floribunda type which bears flowers of more double form and having good fragrance, as compared with those commonly found in this class. This objective was fully achieved, along with other desirable improvements, as evidenced by the following unique combination of characteristics which are outstanding in the new variety and which distinguish it from its parents, as well as from all other varieties of which I am aware:

(1) A vigorous, upright and bushy habit of plant growth;

(2) Good hardiness;

(3) Constant production of healthy, leathery foliage;

(4) Good flower size, averaging 3½ inches in diameter when fully expanded;

(5) Very double flower petalage;

(6) A very strong geranium fragrance which is quite uncommon in floribunda roses;

(7) A distinctive and attractive general color tonality of the flowers corresponding to Scarlet Red lightly overcast with Scarlet; and (8) Long-lasting flower qualities.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Geranium Red" × "Fashion."

*Pollen parent.*—An unnamed seedling of "Diamond Jubilee" × "Fashion."

Classification:

*Botanic.*—Floribunda.

*Commercial.*—Floribunda.

*Flower*

(Observations made from specimens grown outdoors at Newark, New York, near mid-afternoon during the latter part of the month of September.)

Blooming habit: Recurrent—continuous.

Bud:

*Size.*—Large.

*Form.*—Ovoid; is not affected by wet or hot weather.

*Color.*—When sepals first divide—Carmine, Plate 1. When petals begin to unfurl—Spectrum Red, Plate 1, very lightly overcast with Rose Red, Plate 12. When half-blown: inside of petals—Scarlet Red, Plate 1, lightly overcast with Spectrum Red, Plate 1; reverse of petals—Rose Red, Plate 12, lightly overcast with Scarlet Red, Plate 1.

*Sepals.*—Slightly branched; curl back when petals begin to unfurl. Color: inside—Roman Green, Plate 16; outside—Chrysolite Green, Plate 31.

*Calyx.*—Color—Oil Green, Plate 5. Shape—funnel. Size—small. Aspect—smooth. Odor when rubbed—none.

*Peduncle.* — Length — medium. Aspect — rough. Strength—erect; heavy. Color—Oil Green, Plate 5.

*Opening.*—Opens up well; is not affected by adverse weather conditions.

Bloom:

*Size.*—Medium. Average size when fully expanded—3½ inches.

*Borne.*—Both singly and several together.

*Stems.*—Medium length; strong.

*Form (when first open).*—Cupped. Permanence—retains its form to the end.

*Petalage.*—Double (full but open center). Number of petals under normal conditions—from 55 to 60.

*Color.*—Center of flower—Scarlet Red, Plate 1, very lightly overcast with Scarlet, Plate 1. Outer petals—Scarlet, Plate 1, lightly overcast with Scarlet Red, Plate 1. Base of petals (aiglet)—Naphthalene Yellow, Plate 16. Inside of petals—Scarlet Red, Plate 1, lightly overcast with Scarlet, Plate 1. Reverse of petals—Scarlet Red, Plate 1, lightly overcast with Rose Red, Plate 12. General tonality from a distance—Scarlet Red, Plate 1, lightly overcast with Scarlet, Plate 1.

*Discoloration.*—General tonality at end of first day—Scarlet Red, Plate 1, lightly overcast with Scarlet, Plate 1. Second day—Scarlet Red, Plate 1, lightly overcast with Scarlet, Plate 1. Third day—Scarlet, Plate 1, lightly overcast with Scarlet Red, Plate 1.

Petals:

*Texture.*—Leathery; is not affected by wet or hot weather.

*Appearance.*—Inside—satiny. Outside—shiny.

*Form.*—Round.

*Arrangement.*—Imbricated (regularly arranged shingle-like).

*Petaloids in center.*—Few; large.

*Persistence.*—Drops off cleanly.

*Fragrance.*—Strong. Nature—geranium fragrance.

*Lasting quality.*—On the plant — long. As cut flower—long.

*Genital organs*

Stamens, anthers: Medium size; many; regularly arranged around styles. Color—Apricot Yellow, Plate 4.

Stamens, filaments (threads): Medium length. Color—Empire Yellow, Plate 4.

Pollen: Color—Pale Lemon Yellow, Plate 4.

Styles: Loosely separated; uneven length; medium length; thin.

Stigmas: Color—Barium Yellow, Plate 16.

Ovaries: All enclosed in calyx.

Hips: None.

Seeds: None.

*Plant*

Form: Bush.

Growth: Vigorous; upright; bushy; hardy.

Foliage: Compound of 3–7 leaflets.

*Size.*—Medium.

*Quantity.*—Normal.

*Color.*—New foliage: upper side—Mahogany Red, Plate 2, lightly overcast with Yellowish Oil Green, Plate 5; under side—Parrot Green, Plate 5, lightly overcast with Mahogany Red, Plate 2. Old foliage: upper side—Varley's Green, Plate 18; under side—Light Bice Green, Plate 17.

*Shape.*—Oval pointed.

*Texture.*—Upper side—leathery; healthy. Under side—smooth.

*Ribs and veins.*—Ordinary.

*Edge.*—Serrated (saw toothed).

*Serration.*—Single; small.

*Leaf stem.*—Color—Lettuce Green, Plate 5. Under side—smooth.

*Stipules.*—Medium length; smooth.

Wood:

*New wood.*—Color—Lettuce Green, Plate 5. Bark—smooth.

*Old wood.*—Color—Spinach Green, Plate 5. Bark—smooth.

Thorns:

*Thorns.*—Quantity: on main stalks from base—ordinary; on laterals from stalk—ordinary. Form—narrow base; medium length; hooked downward. Color (when young)—Old Rose, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a vigorous, upright and bushy habit of plant growth, good hardiness, constant production of healthy leathery foliage, good flower size, very double flower petalage, a very strong and unusual geranium flower fragrance, a distinctive and attractive general color tonality of the flowers corresponding to Scarlet Red, lightly overcast with Scarlet, and long-lasting flower qualities.

No references cited.